United States Patent
Drewes et al.

(10) Patent No.: US 9,271,974 B2
(45) Date of Patent: Mar. 1, 2016

(54) USE OF OXYCODONE FOR TREATING VISCERAL PAIN

(71) Applicant: PURDUE PHARMA L.P., Stamford, CT (US)

(72) Inventors: Asbjorn Mohr Drewes, Silkeborg (DK); Lars Arendt Nielsen, Aalborg (DK)

(73) Assignee: PURDUE PHARMA L.P., Stamford, CT (US)

( * ) Notice: Subject to any disclaimer, the term of this patent is extended or adjusted under 35 U.S.C. 154(b) by 0 days.

(21) Appl. No.: 14/515,216

(22) Filed: Oct. 15, 2014

(65) Prior Publication Data
US 2015/0190393 A1      Jul. 9, 2015

Related U.S. Application Data

(63) Continuation of application No. 11/814,020, filed as application No. PCT/EP2006/050252 on Jan. 17, 2006, now abandoned.

(60) Provisional application No. 60/645,490, filed on Jan. 18, 2005.

(51) Int. Cl.
*A61K 31/33* (2006.01)
*A61K 31/485* (2006.01)
*A61K 9/00* (2006.01)

(52) U.S. Cl.
CPC .............. *A61K 31/485* (2013.01); *A61K 9/0095* (2013.01)

(58) Field of Classification Search
None
See application file for complete search history.

(56) References Cited

PUBLICATIONS

Riviere (Brit J Pharmcol 141:1331-1334, 2004).*

* cited by examiner

*Primary Examiner* — Craig Ricci
(74) *Attorney, Agent, or Firm* — Troutman Sanders LLP

(57) ABSTRACT

It is possible to effectively treat moderate to severe visceral pain by administering analgesic medications comprising the opioid oxycodone or pharmaceutically acceptable salts thereof. Visceral pain and especially acute (i.e. non-chronic) visceral pain can be effectively treated by administering oxycodone at a dosage which is lower than the corresponding dosage of the other opioids like morphine.

19 Claims, 2 Drawing Sheets

USE OF OXYCODONE FOR TREATING VISCERAL PAIN

CROSS-REFERENCE TO RELATED APPLICATIONS

This application is a continuation of U.S. application Ser. No. 11/814,020 filed May 2, 2008, which is a U.S. national phase of International Application No. PCT/EP2006/050252, filed Jan. 17, 2006, which claims priority from U.S. Provisional Application No. 60/645,490, filed Jan. 18, 2005. The disclosures of all of these prior applications are incorporated herein by reference in their entireties.

FIELD OF INVENTION

The present invention refers to the treatment of visceral pain.

BACKGROUND

There is a continuing need for analgesic medications which are suitable for effectively treating visceral pain and especially acute visceral pain. Deep pain from the internal organs is a common cause of visits to doctors and long-term sick leave in the western world. The causes for visceral pain can be sought in both organic and functional conditions, but what is common to these is that there is complex activation of the nervous system. In many cases, the visceral pain persists despite the original cause having been wholly or partially eliminated. In many cases morphine is currently used for the treatment of moderate to severe visceral pain.

There is also a continuing need for analgesic medications able to provide high efficacy pain relief while reducing the possibility of undesirable effects. Accordingly, it is most desirable to have analgesic medications which provide high efficacy pain relief at low dosages in order to avoid or at least reduce undesirable effects and especially side-effects observed at higher dosages or for certain specific analgesics.

Although opioids are prescribed with increasing frequency, knowledge of their effect on visceral pain is limited. However, it is known that, in addition to analgesic effects, morphine may also cause a number of undesirable effects, including, for example, respiratory depression, nausea, vomiting, dizziness, mental clouding, dysphoria, pruritus, constipation, increased biliary tract pressure, urinary retention and hypotension.

The effect of certain active agents on patients is highly variable. Visceral pain differs from pain in the skin in many ways and is often more difficult to treat.

In the literature different types of pain associated with disease of the viscera are suggested. These types comprise true or localized visceral pain, referred visceral pain, localized parietal pain, and referred parietal pain. The present invention especially refers to the treatment of true or localized visceral pain.

True visceral pain often occurs early in the disease and is characterized by a vague, diffuse, dull, aching pain, which is localized but can have a tendency to radiate. It can be accompanied by a feeling of malaise, and, when severe, it induces strong autonomic phenomena such as sweating, vasomotor responses, bradycardia, nausea and vomiting, and sometimes an alarm reaction. It is usually felt in the midline and deep in the body.

There are a variety of conditions in which visceral pain may exist. For example, pancreatitis pain, labor pain, pain from abdominal surgery associated with ileus, pain in irritable bowel syndrome, abdominal pain in nonulcer dyspepsia, or in dysmenorrhea. Likewise, liver pain, kidney pain, epigastric pain, pleural pain, and painful biliary colic, appendicitis pain may all be considered to be visceral pain. Substernal pain or pressure from early myocardial infarction is also visceral. Diseases of the stomach, dudenum or colon can cause visceral pain. And there are more.

According to an embodiment of the present invention it has been found that it is possible to effectively treat moderate to severe visceral pain by administering analgesic medications comprising the opioid oxycodone or pharmaceutically acceptable salts thereof. Moreover, it has been found that visceral pain and especially acute (i.e. non-chronic) visceral pain can be effectively treated by administering oxycodone at a dosage which is lower than the corresponding dosage of other opioids like morphine. Accordingly, the present invention inter alia refers to a method of effectively treating moderate to severe visceral pain by administering oxycodone at relatively low dosages.

According to an embodiment of the present invention it has been found that treating visceral pain with a specific dosage of oxycodone is more effective than treating the same visceral pain with a higher corresponding dosage of morphine, whereas almost the same effect is observed if cutaneous or muscular pain is treated by administering corresponding dosages of oxycodone or morphine. In other words, according to the present invention it has been found that visceral pain and especially acute moderate to severe visceral pain can be effectively treated by administering oxycodone at relatively low dosages, whereas the "corresponding dosage" of morphine would be less effective in treating the same visceral pain. According to the present invention the "corresponding dosage" of morphine does not mean the same quantitative amount of morphine, but refers to the usual equipotent amount of morphine, i.e. to the amount of morphine which usually provides a similar pain relief to the patient. The usual equipotent weight ratio of morphine to oxycodone for oral administration is about 2:1 (the corresponding molar ratio is about 1.8:1).

According to another embodiment of the invention a method of selectively treating moderate to severe visceral pain in a patient is provided, the method comprising administering oxycodone in an effective amount to provide analgesia in the patient in need thereof. The present invention for the first time allows for the selective treatment of moderate to severe visceral pain, since it was not known prior to the present invention that this specific pain can be effectively treated by administering oxycodone at low dosages, whereas other opioids (like morphine) at dosages, which would have been considered equipotent by the skilled person, are less effective. Patients suffering exclusively from acute visceral pain, according to the present invention would not or no longer be treated with the opioids commonly used for this purpose (like morphine, hydromorphone, oxymorphone, codeine, and hydrocodone) but with oxycodone. Accordingly, the present invention opens a new therapeutic window for the opioid oxycodone.

According to another embodiment of the invention a method of treating moderate to severe visceral pain in a patient already being treated with morphine or a salt thereof is provided, the method comprising:

(a) discontinuing treatment with morphine; and
(b) administering oxycodone or a salt thereof in an amount of less than 50% by weight of the morphine or salt thereof.

According to another embodiment of the invention a method of treating moderate to severe visceral pain in a patient already being treated with hydromorphone, oxymorphone, codeine, hydrocodone or salts thereof is provided, the method comprising:

(a) discontinuing treatment with hydromorphone, oxymorphone, codeine, hydrocodone or salts thereof; and (b) administering oxycodone or a salt thereof in an amount of less than the equipotent weight of the hydromorphone, oxymorphone, codeine, hydrocodone or salts thereof.

An embodiment of the present invention also allows the treatment of acute visceral pain by administering oxycodone at a dosage which is sufficiently low in order to reduce or avoid undesired side effects. This means, that therapeutic levels can be achieved without or with fewer concurrent side effects, such as nausea, vomiting, constipation and drowsiness, which may be associated with high blood levels of oxycodone.

The finding that visceral pain can be effectively treated by administering low dosages of oxycodone allows for the use of immediate release formulations and sustained release formulations. It may be preferred according to the present invention to treat visceral pain and especially acute visceral pain by administering oxycodone-containing once-a-day, twice-a-day, three-times-a-day, or four-times-a-day dosage forms. According to the present invention it may be especially preferred to use oxycodone-containing sustained release formulations, wherein the dosage does not exceed 40 mg oxycodone, preferably does not exceed 30 mg oxycodone and even more preferably does not exceed 10 mg oxycodone. According to the present invention it may be most preferred to use oxycodone-containing sustained release formulations and preferably once-a-day, twice-a-day, three-times-a-day, or four-times-a-day dosage forms comprising about 10 mg, about 9 mg, about 8 mg, about 7 mg, about 6 mg or about 5 mg oxycodone. It is also preferred in certain embodiments to use single-entity oxycodone or salts thereof, e.g., oxycodone or salts thereof without APAPs or other active agents.

SUMMARY

The present invention relates to the treatment of visceral pain including pancreatitis pain, labor pain, pain from abdominal surgery associated with ileus, pain in irritable bowel syndrome, abdominal pain in nonulcer dyspepsia, or in dysmenorrhea, liver pain, kidney pain, epigastric pain, pleural pain, and painful biliary colic and appendicitis pain by administering analgesic medications comprising the oxycodone alone or in combination with other active agents and especially other analgesics. Furthermore, the present invention refers to the treatment of visceral pain resulting from diseases of the stomach, dudenum or colon, from Crohn's disease, pain of the gall bladder, severe menstruational pain, and certain post operative pain conditions. The present invention also relates to the treatment of moderate, moderately severe, and/or severe visceral pain.

The dosage form to be used for treating visceral pain according to the present invention preferably is an oral dosage form like a tablet or capsule, but could also be a suppository or any other solid or liquid dosage form which can be administered orally, via implant, parenterally, sublingually or rectally. Preferably, the formulation in accordance with the present invention is an oral tablet, capsule, or in any other suitable oral unit dosage form.

According to the present invention, visceral pain can be treated by administering oxycodone or a pharmaceutically acceptable salt thereof. The phrase "pharmaceutically acceptable salt" includes, but is not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N-dibenzylethylenediamine salt and the like; inorganic acid salts such as hydrochloride, hydrobromide, sulfate, phosphate and the like; organic acid salts such as formate, acetate, trifluoroacetate, maleate, fumarate, tartrate and the like; sulfonates such as methanesulfonate, benzenesulfonate, p-toluenesulfonate, and the like; amino acid salts such as arginate, asparginate, glutamate and the like.

The Oxycodone-containing formulations which are suitable for treating visceral pain according to the present invention can be immediate release formulations or sustained release formulations. It may be preferred to use sustained release formulations for treating visceral pain and it may be especially advantageous to administer once-a-day, twice-a-day, three-times-a-day, or four-times-a-day dosage forms comprising oxycodone.

In certain embodiments such oral dosage form includes a sustained-release material which is incorporated into a matrix along with the oxycodone or pharmaceutically acceptable salt thereof to provide for the sustained release of the oxycodone. The sustained-release material may be hydrophobic or hydrophilic as desired. The oral dosage form may be prepared as granules, spheroids, matrix multiparticulates, etc. which comprise oxycodone or a pharmaceutically acceptable salt thereof in a sustained release matrix, which may be compressed into a tablet or encapsulated. The oral dosage form may optionally include other pharmaceutically acceptable ingredients (e.g., diluents, binders, colorants, lubricants, etc.).

A non-limiting list of suitable sustained-release materials which may be included in a sustained-release matrix of a dosage form which may be used for treating visceral pain according to the present invention include hydrophilic and/or hydrophobic materials, such as gums, cellulose ethers, acrylic resins, protein derived materials, waxes, shellac, and oils such as hydrogenated castor oil and hydrogenated vegetable oil. However, any pharmaceutically acceptable hydrophobic or hydrophilic sustained-release material which is capable of imparting sustained-release of the oxycodone or pharmaceutically acceptable salt thereof may be used in accordance with the present invention. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, ethyl acrylate, trimethyl ammonioethyl methacrylate, cyanoethyl methacrylate, aminoalkyl methacrylate copolymer, poly (acrylic acid), poly (methacrylic acid), methacrylic acid alkylamine copolymer, poly (methyl methacrylate), poly (methacrylic acid) (anhydride), polymethacrylate, polyacrylamide, poly (methacrylic acid anhydride), and glycidyl methacrylate copolymers.

Oxycodone-containing formulations which may be used for treating visceral pain according to the present invention, for example, are described in WO 02/087512 and EP 0 576 643, both incorporated herein by reference.

EP 0 576 643 refers to a solid, controlled release, oral dosage form, the dosage form comprising a therapeutically effective amount of oxycodone or a salt thereof in a matrix.

The oral dosage forms described in EP 0 576 643 may be especially suitable for the present invention. The dosage forms according to EP 0 576 643 include "twice-a-day" formulations. The oral dosage form may be presented as, for example, granules, spheroids or pellets in a capsule or in any other suitable solid form.

According to the present invention it may preferred that the oral dosage form contains between 1 and 50 mg, preferably between 1 and 15 mg, more preferably between 5 and 10 mg and especially about 5 mg of oxycodone hydrochloride. Alternatively the dosage form may contain the same or molar equivalent amounts of other oxycodone salts or of the oxycodone base.

The matrix of the dosage form to be used for treating visceral pain according to the present invention may preferably be a controlled release matrix, although also normal release matrices having a coating that controls the release of the drug may be used. Suitable materials for inclusion in a controlled release matrix comprise (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The dosage form may contain between 1% and 80% (by weight) of at least one hydrophilic or hydrophobic polymer.

(b) Digestible, long chain (C8-C50, especially C12-C40), substituted or unsubstituted hydrocarbons, such as fatty acids, fatty alcohols, glyceryl esters of fatty acids, mineral and vegetable oils and waxes. Hydrocarbons having a melting point of between 25° C. and 90° C. are preferred. Of these long chain hydrocarbon materials, fatty (aliphatic) alcohols are preferred. The dosage form may contain up to 60% (by weight) of at least one digestible, long chain hydrocarbon.

(c) Polyalkylene glycols. The dosage form may contain up to 60% (by weight) of at least one polyalkylene glycol.

One particular suitable matrix comprises at least one water soluble hydroxyalkyl cellulose, at least one C12-C36, preferably C14-C22, aliphatic alcohol and, optionally, at least one polyalkylene glycol.

The at least one hydroxyalkyl cellulose may preferably be a hydroxyl (C1 to C6) alkyl cellulose, such as hydroxypropylcellulose, hydroxypropylmethylcellulose and, especially, hydroxyethyl cellulose. The amount of the at least one hydroxyalkyl cellulose in the oral dosage form will be determined, inter alia, by the precise rate of oxycodone release required. Preferably however, the oral dosage form contains between 5% and 25%, especially between 6.25% and 15%. (by wt) of the at least one hydroxyalkyl cellulose.

The at least one aliphatic alcohol may be, for example, lauryl alcohol, myristyl alcohol or stearyl alcohol. In particularly preferred embodiments, however, the at least one aliphatic alcohol is cetyl alcohol or cetostearyl alcohol. The amount of the at least one aliphatic alcohol in an oral dosage form will be determined by the precise rate of oxycodone release required.

According to another preferred embodiment, the controlled release composition may comprise from about 5 to about 25% acrylic resin and from about 8 to about 40% by weight aliphatic alcohol by weight of the total dosage form. A particularly preferred acrylic resin comprises Eudragit® RS 30D commercially available from Rohm Pharma.

In addition to the above ingredients, a controlled release matrix may also contain suitable quantities of other materials, e.g. diluents, lubricants, binders, granulating aids, colorants, flavorants and glidants that are conventional in the pharmaceutical art.

As an alternative to a controlled release matrix, the dosage form to be used for treating visceral pain may comprise a normal release matrix having a coat that controls the release of the drug. In particularly preferred embodiments of this aspect of the invention, the dosage form may comprise film coated spheroids containing active ingredient and a non-water soluble spheronising agent. The term spheroid is known in the pharmaceutical art and means a spherical granule having a diameter of between 0.5 mm and 2.5 mm especially between 0.5 mm and 2 mm. Details with respect to film coated spheroids and the manufacture of the above-mentioned dosage forms are also described in EP 0 576 643, incorporated herein by reference.

Controlled release oxycodone-containing formulations which may be especially suitable for treating visceral pain according to the present invention may comprise oxycodone hydrochloride, lactose (spray dried), Povidone, Eudragit® RS 30 D (solids), Triacetin®, stearyl alcohol, talc and magnesium stearate.

Further sustained release formulations containing oxycodone and being suitable for treating visceral pain according to the present invention are described in WO 02/087512, incorporated herein by reference.

According to the present invention, it may be preferred to use a dosage form providing an analgesic effect for at least about 24 hours after oral administration at steady; and the dosage form providing a mean C24/Cmax oxycodone ratio of 0.6 to 1.0 after oral administration at steady state to the patients. In certain embodiments of the invention, the dosage form after administration to patients may provide a mean $T_{max}$ of oxycodone in-vivo which occurs at about 2 to about 17 hours (e. g., about 2 to about 8 hours) after administration at steady state of the dosage form. The term "mean" for purposes of the present invention, when used to define a pharmacokinetic value (e. g., $T_{max}$) represents the arithmetic mean value measured across a patient population. In certain embodiments of the invention, the mean $T_{max}$ of oxycodone in-vivo may occur at about 6.5 hours to about 17 hours, at about 8 to about 16 hours, at about 10 to about 16 hours, or at about 12 to about 16 hours after administration at steady state of the dosage form. The term "steady state" means that the amount of the drug reaching the system is approximately the same as the amount of the drug leaving the system. Thus, at "steady state", the patient's body eliminates the drug at approximately the same rate that the drug becomes available to the patient's system through absorption into the blood stream.

In certain embodiments the sustained release oral dosage form which may be used for treating visceral pain according to the present invention comprises a matrix which includes a sustained release material and oxycodone or a pharmaceutically acceptable salt thereof. In certain embodiments, the matrix is compressed into a tablet and may be optionally overcoated with a coating that in addition to the sustained release material of the matrix may control the release of the oxycodone or pharmaceutically acceptable salt thereof from the formulation, such that blood levels of active ingredient are maintained within the therapeutic range over an extended period of time. In certain alternate embodiments, the matrix may be encapsulated.

In certain embodiments the sustained release oral dosage form to be used according to the present invention can be an osmotic dosage form which comprises a single layer or bilayer core comprising oxycodone or a pharmaceutically acceptable salt thereof; an expandable polymer; a semipermeable membrane surrounding the core; and a passageway disposed in the semipermeable membrane for sustained release of the oxycodone or pharmaceutically acceptable salt thereof, such that blood levels of active ingredient are maintained within the therapeutic range over an extended period of time when administered to patients.

In certain embodiments the sustained release oral dosage form to be used according to the present invention comprises a substantially homogenous core comprising oxycodone or a pharmaceutically acceptable salt thereof and an expandable polymer; a semipermeable membrane surrounding the core; and a passageway disposed in the semipermeable membrane for sustained release of the oxycodone or pharmaceutically acceptable salt thereof, such that blood levels of active ingredient are maintained within the therapeutic range over an extended period of time when administered to a patients.

Another sustained release oral analgesic dosage form which may be suitable for the use according to the present invention is described in EP 1 449 531, incorporated herein by reference. Said dosage form comprises a combination of a pharmaceutical extrudate in the form of multiparticulates including 5 mg to 400 mg oxycodone or a salt thereof dispersed in a matrix. EP 1 449 531 is also related in part to a new melt-extruded oral sustained-release dosage forms which comprise a pharmaceutically acceptable hydrophobic material, a retardant selected from waxes, fatty alcohols, and fatty acids, and a drug. The extrudate can be divided into unit doses of the opioid analgesic. The unit doses of multiparticulates may then be incorporated into a solid pharmaceutical dosage formulation, e.g. via compression or shaping into tablets, by placing a requisite amount inside a gelatin capsule, or by forming the extruded product into the form of a suppository.

Further controlled release matrices or controlled release dosage forms which may be suitable according to the present invention are described in the following documents:

EP 0 548 448, incorporated herein by reference, refers to a stabilized solid controlled release dosage form having a coating derived from an aqueous dispersion of ethylcellulose is obtained by overcoating a substrate including a therapeutically active with an aqueous dispersion of ethylcellulose and then curing the coated substrate at a temperature and relative humidity elevated to a suitable level above ambient conditions until the coated dosage form attains a stabilized dissolution profile substantially unaffected by exposure to storage conditions of elevated temperature and/or elevated relative humidity.

EP 0 531 611 incorporated herein by reference, refers to a controlled release dosage form having a matrix of sodium alginate and a calcium salt. When the composition is to be administered rectally, the matrix is combined with a therapeutically active agent and a suitable suppository base. When the composition is to be administered orally, the matrix further includes a higher aliphatic alcohol.

EP 0 553 392, EP 0 630 646 and EP 0 636 366 refer to controlled release dosage forms having certain coatings. EP 0 647 448 and EP 0 698 389 also refer to orally administrable opioid formulations providing controlled or sustained release of the active agent. Each of the foregoing documents is incorporated herein by reference.

Once-a-day sustained release opioid formulations are disclosed in U.S. Pat. Nos. 5,478,577; 5,672,360; 5,958,459; 6,103,261; 6,143,322; 5,965,161; 5,958,452 and 5,968,551, all incorporated by reference herein.

Moreover, there are also commercially available oxycodone-containing oral preparations which may be used for treating visceral pain according to the present invention. These commercially available oxycodone-containing preparations include Oxynorm® (immediate release preparation) and OxyContin®. OxyContin is a controlled release analgesic, which is commercially available from Purdue Pharma L.P. OxyContin® is available in 10 mg, 20 mg, 40 mg, and 80 mg dosage strengths. OxyContin is also commercially available in the U.K by Napp Pharmaceuticals in a 5 mg dosage strength. According to the present invention low dosage preparations may be preferred. Dosage forms having an Oxy-Contin®-like matrix and comprising about 5 mg of oxycodone hydrochloride may be especially preferred It may be preferred according to the present patent application to provide a dosage form which comprises a combination of opioid agonist and opioid antagonist in order to reduce or prevent the abuse potential. Suitable dosage forms comprising combinations of opioid agonist and opioid antagonist are described, for example, in WO 99/32119, WO 99/32120, WO 01/58447, WO 03/013479 and WO 03/013476.

Subsequently, it is referred to different aspects of the present invention. However, it is to be understood that the present invention is not limited to these aspects.

It should be understood that for purposes of the present invention, the following terms have the following meanings:

The term "visceral pain" is defined for purposes of the present invention as referring to pain within the viscera of the human body and especially to pain from the internal organs.

The term "acute visceral pain" is defined for purposes of the present invention as referring to visceral pain which is not chronic.

The term "effective" in connection with the analgesic effect is defined for purposes of the present invention as a satisfactory reduction in or elimination of pain, along with the process of a tolerable level of side effects, as determined by the human patient.

The term "selectively treating" is defined for purposes of the present invention as referring to the selective use of oxycodone for effectively treating a specific pain, namely acute visceral pain. The treatment of visceral pain with e.g. morphine would also lead to some analgesic effect, but would not be considered "selective" since such analgesic effect would be significantly lower in comparison to oxycodone and would also be observed for other pain. In other words, no selective effect would be observed for the treatment of visceral pain with morphine.

The present invention includes the following aspects:

According to one aspect of the present invention, a method of effectively treating visceral pain is provided which comprises administering oxycodone at a dosage which is sufficiently low in order to reduce or avoid undesired side effects.

According to another aspect of the present invention, a method of effectively treating visceral pain is provided which comprises administering a oxycodone-containing dosage form, wherein the dosage form provides immediate release or sustained release of the oxycodone.

According to another aspect of the present invention, a method of effectively treating visceral pain is provided which comprises administering oxycodone at a dosage which provides a significantly better effect than the orally equipotent dosage of morphine or other opioid, wherein the equipotency refers to the treatment of cutaneous and muscular pain.

According to a further aspect of the present invention, a method of selectively treating acute visceral pain in a patient is provided, the method comprising orally administering oxycodone in an effective amount to provide analgesia in a patient in need thereof.

According to another embodiment of the invention a method of treating moderate to severe visceral pain in a patient already being treated orally with morphine or a salt thereof is provided, the method comprising:

(a) discontinuing oral treatment with morphine; and (b) orally administering oxycodone or a salt thereof in an amount of less than 50% by weight of the morphine or salt thereof. It may be preferred to orally administer oxycodone or a salt thereof in an amount of less than less than 45% by weight, preferably less than 40% by weight, more preferably less than 35% by weight, even more preferably less than 30% by weight and most preferred 25% by weight of the morphine or salt thereof.

Furthermore, the present invention includes the following aspects:

A method of treating acute visceral pain by administering oxycodone at a dosage which is lower than the corresponding dosage of morphine required for providing the same therapeutic effect.

A method of treating visceral pain by administering oxycodone at a dosage which is lower than the corresponding dosage of morphine required for treating the same visceral pain as efficiently.

A method for effectively treating visceral pain by orally administering oxycodone at a dosage which is lower than the equipotent dosage of oral morphine, wherein the equipotency refers to the treatment of cutaneous and muscular pain. The weight ratio of the aforementioned dosage of oxycodone to the aforementioned dosage of morphine is preferably less than 1:2, more preferably less than 1:2.5, even more preferably less than 1.3 and most preferably less than 1.4

Use of oxycodone or a pharmaceutically acceptable salt thereof for the manufacture of a medicament for treating visceral pain.

Use of oxycodone or a pharmaceutically acceptable salt thereof, wherein oxycodone or a pharmaceutically acceptable salt thereof is used for the manufacture of a medicament for treating acute visceral pain.

Use of oxycodone or a pharmaceutically acceptable salt thereof, wherein oxycodone or a pharmaceutically acceptable salt thereof is used for the manufacture of a medicament for selectively treating visceral pain.

Use of oxycodone or a pharmaceutically acceptable salt thereof, wherein the medicament is an oral dosage form containing oxycodone or a pharmaceutically acceptable salt thereof.

Use of an oral controlled dosage form for the manufacture of a medicament to control visceral pain in human patients, the oral controlled release dosage form comprising:
  a) from 5 mg to 80 mg oxycodone or a salt thereof;
  b) an effective amount of a controlled release acrylic resin matrix, said acrylic resin matrix being selected so that the formulation provides substantially pH-independent in-vitro dissolution characteristics;
  c) a pharmaceutical diluent.

According to the present invention, the term "substantially pH-independent" means that the difference, at any given time, between the amount of oxycodone released at pH 1.2 and the amount released at pH 7.5 (when measured in-vitro using USP Basket Method at 100 rpm in 900 ml aqueous buffer), is 15%, preferably 10% (by weight based on the total amount of oxycodone or salt thereof in the dosage form) or less.

Use of an oral controlled dosage formulation for the manufacture of a medicament to control visceral pain in human patients, the oral controlled release dosage formulation comprising:
  a) about 5 mg oxycodone or a salt thereof;
  b) an effective amount of a controlled release acrylic resin matrix, said acrylic resin matrix being selected so that the formulation provides substantially pH-independent in-vitro dissolution characteristics; and
  c) a pharmaceutical diluent.

Further aspects are described in the claims.

According to another aspect of the invention a method of treating moderate to severe visceral pain in a patient is provided, the method comprising repeatedly administering 5 mg sustained-release oxycodone twice a day, three-times-a-day, or four-times-a-day.

According to another aspect of the invention a method of treating moderate to severe visceral pain in a patient is provided, the method comprising repeatedly administering 10 mg sustained release oxycodone once a day.

It should be understood that the following aspects of the present inventions may be specific or preferred embodiments of the foregoing aspects of the present invention:

According to the present invention it may be preferred that the oxycodone-containing medicament is in the form of a solid oral dosage form like a tablet or capsule.

According to the present invention it may be preferred that the oxycodone-containing oral dosage form provides immediate release of the oxycodone.

According to the present invention it may be preferred that the oxycodone-containing oral dosage form provides sustained release of the oxycodone.

According to the present invention it may be preferred that the oxycodone-containing sustained release dosage form is orally administered on a once daily or twice daily basis.

According to the present invention it may be preferred that the oxycodone-containing medicament comprises oxycodone in an amount of from about 1 mg to about 50 mg, preferably between 1 and 15 mg, more preferably between 5 and 10 mg and especially of about 5 mg or an equivalent amount of pharmaceutically acceptable salt thereof. If the oxycodone-containing medicament is in the form of a sustained release dosage form to be administered on a once daily or twice daily basis, the amount of oxycodone in some cases may be higher and may be in the range from about 5 mg to about 160 mg, but preferably is not exceeding 40 mg, more preferably is not exceeding 20 mg and most preferably is not exceeding 10 mg.

According to another aspect of the invention a method of treating moderate to severe visceral pain in a patient is provided, the method comprising:
  (a) administering to a human patient a unit dose containing oxycodone or a salt thereof in an amount of 5 mg;
  (b) monitoring pharmacodynamic parameters elicited by said unit dose in said human patient and determining whether said pharmacodynamic parameters are appropriate for continued treatment of said patient on a repeated basis;
  (c) titrating the patient by adjusting the dose of oxycodone or a salt thereof administered to the patient by administering a unit dose of oxycodone or a salt thereof with a different amount of oxycodone or a salt thereof if it is determined that said pharmacodynamic parameters are not satisfactory or maintaining the dose of oxycodone or a salt thereof in said unit dose at a previously administered amount if said pharmacodynamic parameters are deemed appropriate;
  (d) continuing the step (c) titration by adjusting the dose of oxycodone or a salt thereof until appropriate steady-state pharmacodynamic parameters are achieved in said patient; and
  (e) continuing the administration of the dose of oxycodone or a salt thereof until treatment is terminated. I may be preferred that the patient is titrated with a unit dose containing oxycodone or a salt thereof in an amount of 5 mg to 10 mg.

According to other embodiments of the present invention, the oxycodone-containing medicament may comprise another active agent, preferably another opioid or nonopioid analgesic agent. Preferred combinations of oxycodone and other active agents are described herein above.

Experimental Evidence

The foregoing is also supported by the experimental evidence referred to below.

The experimental studies referred to below, are based on a comparison of different drugs at healthy volunteers by applying experimental pain, since clinical studies provide insufficient information, partly due to the great difference that exists between patients and partly due to the fact that most diseases produce many symptoms other than pain, which affects the assessment of pain-killing efficacy. Experimental pain can be administered under controlled conditions in healthy volunteers so that this bias can be avoided. However, several experimental stimuli are necessary to simulate the complex clinical situation. It is also necessary to use different opioids to obtain sufficient differentiated knowledge about deep pain on different pain mechanisms, and an assessment of the clinical action spectrum of opioids. For testing the efficacy of different opioids for treating visceral pain a standardized test battery of cutaneous, muscular and visceral stimuli was applied. Blood samples were taken for determination of the opioid concentration in plasma.

In recent years methods by which deep and visceral stimuli can be administered reproducibly have been developed. These methods allow activation of the pain system with different stimuli, with the possibility of activating various types of nerve pathways in the same experiment. In the trial described herein the efficacy of different opioids on different types of stimuli of skin, muscles and bowel in healthy volunteers have been compared. Cutaneous and muscular pain was administered by pressure, current and temperature (skin only). The stimulation of the internal organs was also produced by pressure via a balloon located at the bottom of the oesophagus. The balloon can be distended and produce mechanical stimuli, which feel like mild pain/discomfort. In addition, cold and heat stimuli can be administered by passing water of differing temperature through the balloon.

Aim

The purpose of the present study was to compare the efficacy of two different opioids on different experimental pain models, where the pain induced is very similar to clinical pain. The experimental pain induced must therefore activate different peripheral deep/visceral pain pathways in several organs during controlled conditions. During the trial the intensity of pain was measured as a result of a well-defined pain stimulus consecutively, but the analgesic effect of orally administered opioid is built up.

Each of the experiments was carried out on healthy volunteers and includes 24 individuals aged between 18 and 65, male/female ratio 1:1, without any previous chronic or recurrent diseases causing pain. The subjects have also undergone a physical examination and have been screened for any diseases with testing of urine (dipsticks for protein and sugar) and blood tests (haemoglobin, C-reactive protein, platelelets, leukocytes, creatinine, aspartate aminotransferase, alkaline phosphatase, prothrombin time) before they were included in the study. The duration of each of the sub-trials will be maximum 2 hours. The subjects were included three times, with a minimum of one week between each trial.

Trial Design and Methods

In the series of trials morphine was compared with oxycodone. In addition, both drugs have been compared with a placebo. The drug substances were tested by using experimental pain models including cutaneous, intramuscular and visceral pain stimulation in healthy subjects.

The trials were conducted according to a block-randomised (three blocks), balanced (opioid sequence) double-blind, placebo-controlled cross-over design with three arms (opioids and placebo) and open therapeutic control. Blinding for patients and those giving treatment was undertaken by pouring the medicine together with grape juice (ensuring blinding of placebo) according to the following pattern.

| Opioid | Placebo mg | morphine 30 mg | oxycodon 15 mg |
|---|---|---|---|
| | 100 ml grape juice | 15 ml morphine DAK oral solution 2 mg/ml + 85 ml grape juice | 15 ml Oxynorm oral solution 1 mg/ml + 85 ml grape juice |

At least 7 days pass between each dose, which ensures sufficient wash-out.

Experimental Pain Models/Pain Stimuli

Several separate trials have been performed, where the placebo and the 2 opioids were tested on the experimental pain models. Beforehand a test has been performed in which the subjects have tested the various pain stimuli and have learnt to score them on the scales used (intensity and referred spread of pain). Pain stimuli are given before and during treatment (at the expected maximum effect of the drug). The model was first tested on skin, muscle and oesophageal stimuli. Stimuli with cutaneous, muscular and visceral tests were applied at the various intensities tested for the trial and after 30, 60 and 90 minutes.

The effect of opioids on mechanical stimuli was studied by stimulating skin and muscle with a pressure algometer (Somedia algometer) and by stimulating the oesophagus with a balloon, where the cross-sectional area can be calculated (impedance planimetry). Sensation for electrical stimulations was studied on the skin and in the muscles of the lower arm ("single and repeated stimuli"). It was ensured in this way that both pure peripheral pain and central mechanisms ("repeated stimuli") are studied. The effect of thermal stimuli was measured on the skin of the lower arm (Somedic thermotest) and in the osophagus by warm and cold water perfusing the balloon. A stimulus-response curve was produced for all types of stimuli. The pain intensity was scored on a visual analogue scale (VAS) from 0 (no pain) to 10 (intolerable), which combines non-painful (0-4.9 on the scale) and painful (5-10 on the scale) stimuli. Stimuli with an intensity of 1, 3, 5=pain detection threshold and 7=moderate pain are given.

Kinetics

Blood samples of 10 ml for assessment of the variation in plasma concentration for the opioids were taken from a peripheral venflon for opioid dosage (blank test) and 30, 45, 60, 90 and 120 minutes after dosage. A total of 240 ml blood is therefore taken over the whole trial (4 weeks).

Preparations and Dose

Morphine DAK oral solution 2 mg/ml; Dose 30 mg

Oxynorm oral solution 1 mg/ml; Dose: 15 mg

It was assumed that the equipotent ratio of morphine to oxycodone is about 2:1 by weight.

Statistical Treatment of Data

The pain threshold was determined for the various stimuli before the trial and after 30 min (expected initial effect), 60 and 90 minutes (expected maximum effect). Stimuli were produced at different intensities for stimulation in skin, muscles and oesophagus. Data were stored electronically and entered on CRFs. The analgesic effect before and during the trial was determined by 2-sided variance analysis with the factors 1) either placebo versus morphine or morphine versus oxycodone and 2) intensity or pain stimulus and the dependent variable "pain score". The effect on pain quality was studied by the Danish version of the "McGill Pain Questionnaire" being filled in at maximum pain.

The effect on pain threshold after 90 minutes was counted as the primary endpoint. The other data (effect on other pain intensities, change in the qualitative descriptive words, change in reported area of pain) were regarded as secondary, descriptive variables. The plasma measurements were thus to be regarded as secondary endpoints used in the descriptive phase to support the effect on pain data.

BRIEF DESCRIPTION OF THE DRAWINGS

The invention will be better understood upon reading the following description and examining the accompanying figures. These figures are provided as an illustration, but are not limiting on the invention. These figures are as follows.

DETAILED DESCRIPTION

Results

Figure 1A:
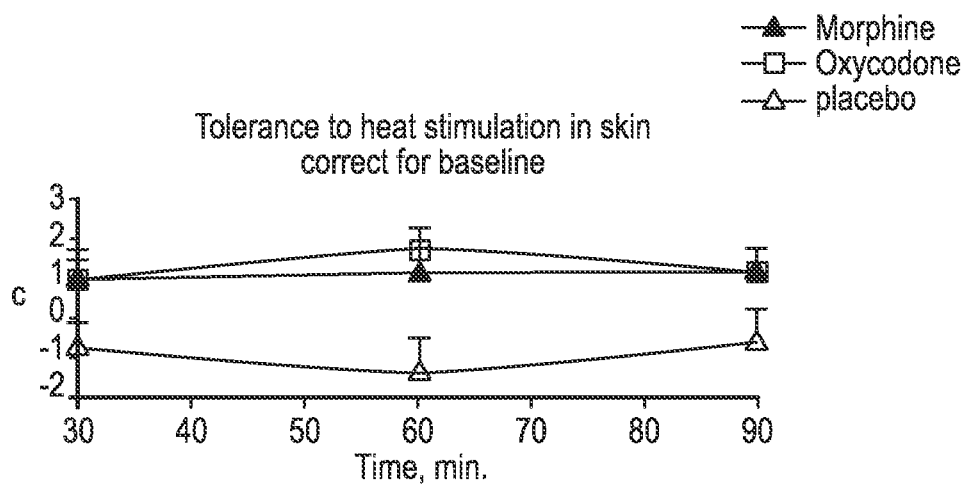
FIG. 1A is a plot comparing the influence of morphine, oxycodone and placebo on tolerance to heat stimulation in skin.
Figure 1B:
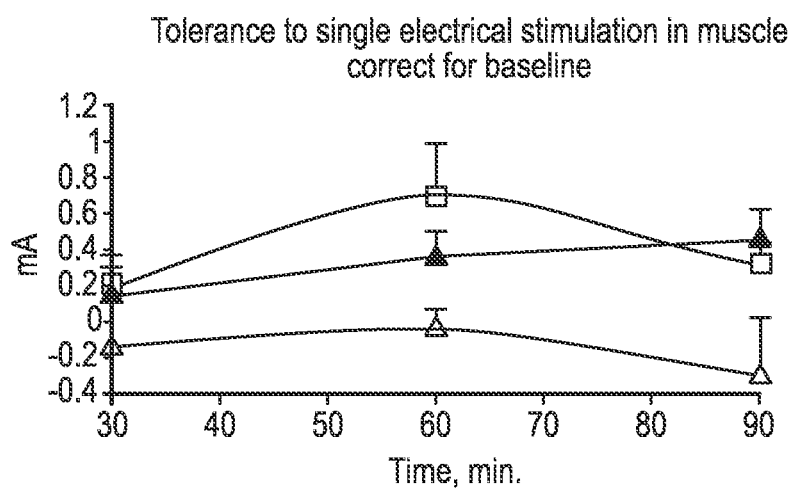
FIG. 1B is a plot comparing the influence of morphine, oxycodone and placebo on tolerance to electrical stimulation in muscle.

In the skin both opioids, morphine and oxycodone, were significantly more analgesic than placebo and there was no significant difference between morphine and oxycodone for all modalities tested (see FIG. 1). Note also that the potency ratio of 2:1 (oxycodone:morphine) was confirmed in this study as being "equipotent" for cutaneous pain. In muscle opioids again were significantly more analgesic than placebo and there was no significant difference between morphine and oxycodone for all modalities tested (see FIG. 1). Note also that the potency ratio of 2:1 (oxycodone:morphine) was confirmed in this study as being "equipotent" for muscular pain.

Figure 2A:
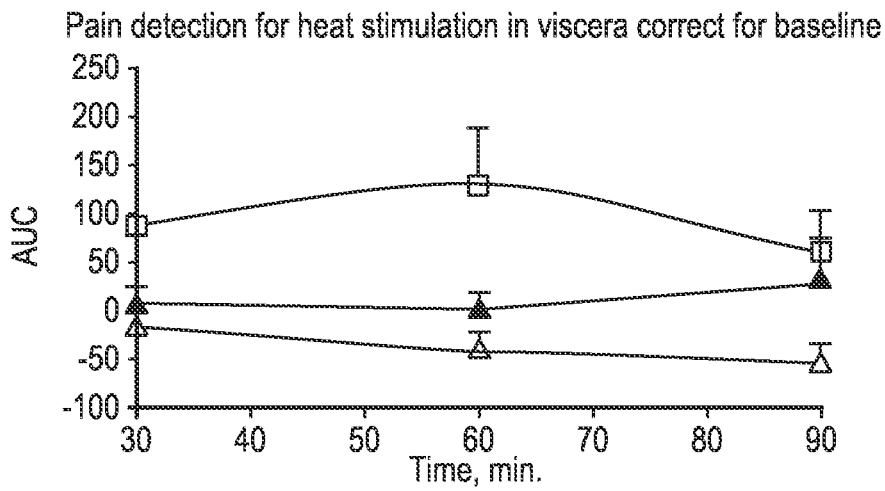
FIG. 2A is a plot comparing the influence of morphine, oxycodone and placebo on pain detection in response to heat stimulation in viscera.
Figure 2B:
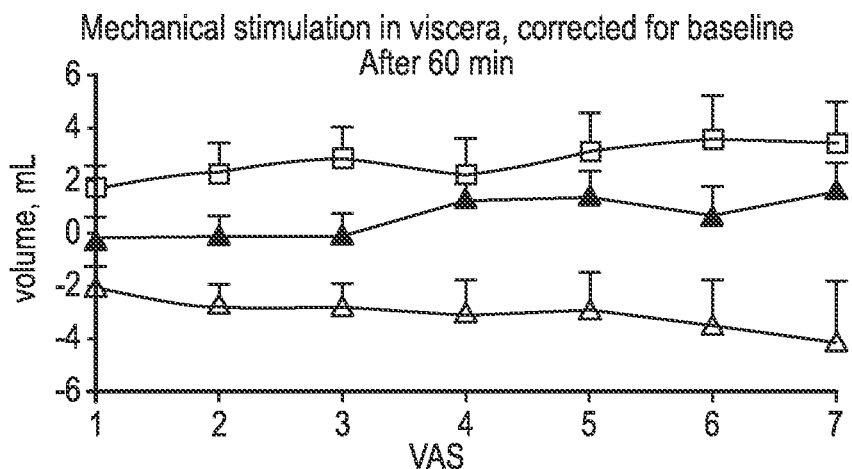
FIG. 2B is a plot comparing the influence of morphine, oxycodone and placebo on mechanical stimulation in viscera.
Figure 3:
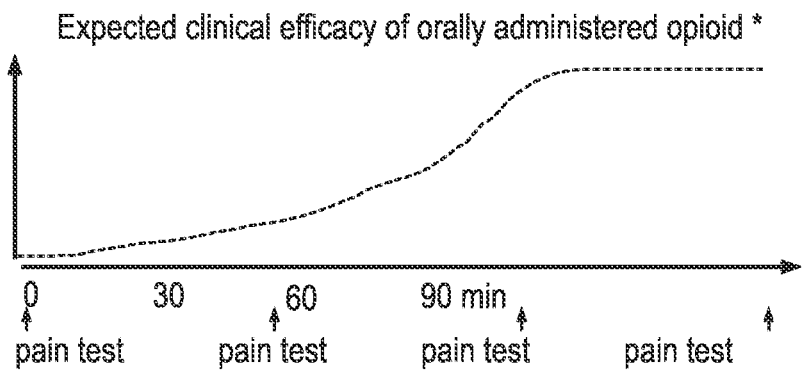
FIG. 3 is a plot comparing the influence of morphine, oxycodone and placebo on mechanical stimulation in viscera.

In viscera (oesophagus here), a in comparison to than morphine and placebo significantly better analgesic effect was observed for oxycodone against mechanical stimulation (via balloon distension) (see FIG. 2). Morphine, however, also provided a certain analgesic effect (in comparison to placebo).

There was also significantly greater analgesia by oxycodone against heat pain stimulation (via hot water into the balloon) in comparison to morphine and placebo (see FIG. 2). Morphine, however, also provided a certain analgesic effect (in comparison to placebo).

The foregoing results clearly confirm that visceral pain and especially acute visceral pain can be effectively and selectively treated by administering oxycodone at a dosage which is lower than the corresponding, i.e. equipotent dosage of other opioids like morphine.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced herein ("herein cited documents") including any manufacturer's instructions, descriptions, product specifications, and product sheets for any products mentioned herein or in any document referenced herein, are hereby incorporated herein by reference, and may be employed in the practice of the invention. Citation or identification of any document in this application is not an admission that such document is available as prior art to the present invention. It is noted that in this disclosure, terms such as "comprises", "comprised", "comprising" and the like can have the meaning attributed to it in U.S. Patent law; e.g., they can mean "includes", "included", "including", and the like.

The invention claimed is:

1. A method of treating acute post-operative visceral pain in a human patient, which method comprises:
    (a) administering to the patient a unit dosage form comprising oxycodone, or a pharmaceutically acceptable salt thereof, without other active opioid analgesic agents;
    (b) monitoring one or more pharmacodynamic parameters elicited by said unit dosage form in the patient;
    (c) adjusting the amount of oxycodone or pharmaceutically acceptable salt thereof in the unit dosage form if the one or more pharmacodynamic parameters are not appropriate for treatment; and
    (d) administering the unit dosage form containing the adjusted amount of oxycodone or pharmaceutically acceptable salt thereof to the patient;
    in which steps of monitoring (b), adjusting (c), and administering (d) are repeated until the pharmacodynamic parameters are appropriate for treatment.

2. A method of treating acute post-operative visceral pain from abdominal surgery associated with ileus in a human patient, which method comprises:
    (a) administering to the patient a unit dosage form comprising oxycodone, or a pharmaceutically acceptable salt thereof, without other active opioid analgesic agents;
    (b) monitoring one or more pharmacodynamic parameters elicited by said unit dosage form in the patient;
    (c) adjusting the amount of oxycodone or pharmaceutically acceptable salt thereof in the unit dosage form if the one or more pharmacodynamic parameters are not appropriate for treatment; and
    (d) administering the unit dosage form containing the adjusted amount of oxycodone or pharmaceutically acceptable salt thereof to the patient;
    in which steps of monitoring (b), adjusting (c), and administering (d) are repeated until the pharmacodynamic parameters are appropriate for treatment of the patient suffering from visceral pain from abdominal surgery associated with ileus.

3. A method according to claim 2, wherein said unit dosage form is administered from one to four times daily.

4. A method according to claim 2, wherein said unit dosage form comprises 1 mg to 50 mg of oxycodone hydrochloride.

5. A method according to claim 2, wherein said unit dosage form comprises 1 mg to 15 mg of oxycodone hydrochloride.

6. A method according to claim 2, wherein said unit dosage form comprises 1 mg to 10 mg of oxycodone hydrochloride.

7. A method according to claim 2, wherein said unit dosage form comprises 5 mg of oxycodone hydrochloride.

8. A method according to claim 2, wherein said unit dosage form comprises 10 mg of oxycodone hydrochloride.

9. A method according to claim 2, wherein said unit dosage form comprises 15 mg of oxycodone hydrochloride.

10. A method according to claim 2, wherein said unit dosage form comprises 30 mg of oxycodone hydrochloride.

11. A method according to claim 2, wherein said unit dosage form comprises 40 mg of oxycodone hydrochloride.

12. A method according to claim 4, wherein said unit dosage form is administered from one to four times daily.

13. A method according to claim 5, wherein said unit dosage form is administered from one to four times daily.

14. A method according to claim 7, wherein said unit dosage form is administered from one to four times daily.

15. A method according to claim 8, wherein said unit dosage form is administered from one to four times daily.

16. A method according to claim 9, wherein said unit dosage form is administered from one to four times daily.

17. A method according to claim 10, wherein said unit dosage form is administered from one to four times daily.

18. A method according to claim 11, wherein said unit dosage form is administered from one to four times daily.

19. A method according to claim 2, wherein the oxycodone or a pharmaceutically acceptable salt thereof is contained in an oral dosage form.

* * * * *